(12) United States Patent
Khoury

(10) Patent No.: US 7,187,964 B2
(45) Date of Patent: Mar. 6, 2007

(54) CARDIAC CATHETER IMAGING SYSTEM

(75) Inventor: Dirar S. Khoury, Dept. of Medicine, Section of Cardiology 6565 Fannin St., M941A, Houston, TX (US) 77030

(73) Assignee: Dirar S. Khoury, Stafford, TX (US)

( * ) Notice: Subject to any disclaimer, the term of this patent is extended or adjusted under 35 U.S.C. 154(b) by 658 days.

(21) Appl. No.: 10/256,188

(22) Filed: Sep. 26, 2002

(65) Prior Publication Data
US 2003/0065271 A1 Apr. 3, 2003

Related U.S. Application Data

(60) Provisional application No. 60/325,707, filed on Sep. 28, 2001.

(51) Int. Cl.
*A61B 5/04* (2006.01)
(52) U.S. Cl. ...................................... 600/509
(58) Field of Classification Search ................ 600/374, 600/508, 509, 523
See application file for complete search history.

(56) References Cited

U.S. PATENT DOCUMENTS

| | | | | |
|---|---|---|---|---|
| 4,649,924 | A | * | 3/1987 | Taccardi ...................... 600/374 |
| 5,409,000 | A | * | 4/1995 | Imran .......................... 600/374 |
| 5,450,846 | A | * | 9/1995 | Goldreyer .................... 600/374 |
| 5,558,093 | A | * | 9/1996 | Pomeranz ..................... 600/439 |
| 5,699,805 | A | * | 12/1997 | Seward et al. ............... 600/459 |
| 5,860,974 | A | | 1/1999 | Abele .......................... 606/41 |
| 5,908,445 | A | * | 6/1999 | Whayne et al. .............. 607/122 |
| 6,078,831 | A | * | 6/2000 | Belef et al. .................. 600/424 |
| 6,839,588 | B1 | * | 1/2005 | Rudy .......................... 600/523 |
| 6,892,091 | B1 | * | 5/2005 | Ben-Haim et al. .......... 600/509 |
| 2001/0000791 | A1 | | 5/2001 | Suorsa et al. ............... 600/439 |
| 2002/0107515 | A1 | * | 8/2002 | Edwards et al. ............. 606/41 |

OTHER PUBLICATIONS

Definition of "measure" from The American Heritage Dictionary, Second College Edition (1982).*
Rao, et al., A Novel Electrical-Anatomical Imaging Catheter that Combines Noncontact Mapping and Intracardiac Echocardiography, Supplement to Circulation Journal of the American Heart Association, Abstracts from Scientific Sessions 2001, vol. 104, No. 17, Oct. 23, 2001, p. 2564.
Benjamin EJ, Wolf PA, Agostino RB, Silbershatz H, Kannel WB, Levy D. Impact of atrial fibrillation on the risk of death: the Framingham Heart Study. Circulation 1998;98:946-952.
Zipes DP and Wellens HJJ. Sudden cardiac death. Circulation 1998;98:2334-2351.

(Continued)

*Primary Examiner*—George Manuel
(74) *Attorney, Agent, or Firm*—Law Offices of Mark L. Berrier

(57) ABSTRACT

A device for measuring parameters of human tissue includes a multielectrode catheter for taking multiple measurements of the electrical characteristics of the human tissue, a concentric tube catheter located inside the multielectrode catheter, for providing structural support to the multi-electrode catheter and for serving as a conduit for advancing or withdrawing the multielectrode catheter over its surface; and an imaging catheter located inside the concentric tube catheter for taking multiple measurements of anatomical characteristics of the human tissue.

44 Claims, 9 Drawing Sheets

OTHER PUBLICATIONS

The Cardiac Arrhythmia Suppression Trial (CAST) Investigators. Effect of encainide and flecainide on mortality in a randomized trial of arrhythmia suppression after myocardial infarction. N Engl J Med 1989;321:406-412.

The ESVEM Investigators. Determinants of predicted efficacy of antiarrhythmic drugs in the electrophysiologic study versus electrocardiographic monitoring trial. Circulation 1993;87:323-329.

Jackman WM, Beckman KJ, McClelland JH, Wang X, Friday KJ, Roman CA, Moulton KP, Twidale N, Hazlitt A, Prior MI, Oren J, Overholt ED, Lazzarra R. Treatment of supraventricular tachycardia due to atrioventricular nodal reentry by radiofrequency catheter ablation of slow-pathway conduction. N Engl J Med 1992;327:313-318.

Calkins H, Yong P, Miller JM, Olshansky B, Carlson M, Saul P, Huang SKS, Liem B, Klein LS, Moser SA, Bloch DA, Gillette P, Prystowsky E, for the Atakr Multicenter Investigators Group. Catheter ablation of accessory pathways, atrioventricular nodal reentrant tachycardia, and the atrioventricular junction: final results of a prospective, multicenter clinical trail. Circulation 1999;99:262-270.

Papageorgiou P, Anselme F, Kirchlof CJHJ, Monahan K, Rasmussen CAF, Epstein LM, Josephson ME. Coronary sinus pacing prevents induction of atrial fibrillation. Circulation 1997;96:1893-1898.

Moss AJ, Hall J, Cannom DS, Daubert JP, Higgins SL, Klein H, Levine JL, Saksena S, Waldo AL, Wilber D, Brown MW, Heo M, for the Multicenter Automatic Defibrillator Implantation Trial Investigators. Improved survival with an implanted defibrillator in patients with coronary disease at high risk for ventricular arrhythmia. N Engl J Med 1996;335:1933-40.

Zhu WX, Maloney JD, Pinski S, Nitta J, Fitzgerald DM, Trohman RG, Khoury DS, Saliba W, Belco KM, Rizo-Patron C, Simmons TW. Efficacy and safety of radiofrequency catheter ablation of symptomatic ventricular ectopy. J Am Coll Cardiol 1995;26:843-849.

Waldo AL, Vitikainen KJ, Hoffman BF. The sequence of retrograde atrial activation in the canine heart. Circ Res 1975;37:156-163.

Walcott GP, Reek S, Klein HU, Smith WM, Ideker RE. Cardiac mapping systems and their use in treating tachyarrhythmias. In Singer I, Barold SS, and Camm AJ (Eds): Nonpharmacological Therapy of Arrhythmias for the 21st Century: The State of the Art. Armonk, NY: Futura Publishing Co, 1998, pp. 591-606 (Missing pp. 592-606).

Chen PS, Moser Km, Dembitsky WP, Auger WR, Daily PO, Calisi CM, Jamieson SW, Feld CK. Epicardial activation and repolarization patterns in patients with right ventricular hypertropy. Circulation 1991;83:104-118.

Konings KTS, Smeets JLRM, Penn OC, Wellens HJJ, Allessie MA. Configuration of unpolar atrial electrograms during electrical induced atrial fibrillation in humans. Circulation 1997;95:1231-1241.

Josephsen ME, Horowitz LN, Spielman SR, Waxman HL, Greespan AM. Role of catheter mapping in the preoperative evaluation of ventricular tachycardia. Am J Cardiol 1982;29:207-220.

Gepstein L, Hayam G, Ben-Haim SA. A novel method for nonfluoroscopic catheter-based electroanatomical mapping of the heart. In vitro and in vivo accuracy results. Circulation 1997;95:1611-1622.

De Groot, N. M.S., Bootsma M, Van Der Velde ET, Schalij MJ. Three-dimensional catheter positioning during radiofrequency ablation in patients: first application of a real-time position management system. J Cardiovasc Electrophysiol 2000;11:1183-1192.

Wittkampf FHM, Wever EFD, Derksen R, Wilde AAM, Ramanna H, Hauer RNW, Robles de Medlina EO. LocaLisa. New technique for real-time 3-dimensional localization of regular intracardiac electrodes. Circulation 1999;99:1312-1317.

Jenkins KJ, Walsh EP, Colan SD, Bergau DM, Saul JP, Lock JE. Multipolar endocardial mapping of the right atrium during cardiac catheterization: description of a new technique. J Am Coll Cardial 1993;22:1105-1110.

Eldar M, Fitzpatrick AP, Ohad D, Smith MF, Hsu S, Whayne JG, Vered Z, Rotstein Z, Kordis T, Swanson DK, Chin M, Scheinman MM, Lesh MD, Greenspon AJ. Percutaneous multielectrode endocardial mapping during ventricular tachycardia in the swine model. Circulation 1996;94:1125-1130.

Taccardi B, Arisi G, Macchi E, Baruffi S, Spaggiari S. A new intracavitary probe for detecting the site of origin of ectopic ventricular beats during one cardiac cycle. Circulation 1987;75:272-281.

Derfus DL, Pilkington TC, Simpson EW, Ideker RE. A comparison of measured and calculated intracavitary potentials for electrical stimuli in the exposed dog heart. IEEE Trans Biomed Eng 1992;39:1192-1206.

Schilling RJ, Peters NS, Davies DW. Simultaneous endocardial mapping in the human left ventricle using a noncontact catheter: Comparison of contact and reconstructed electrograms during sinus rhythm. Circulation 1998;98:887-898.

Barr RC, Spach MS. Inverse calculations of QRS-T epicardial potentials from body surface potential distributions for normal and ectopic beats in the intact dog. Cir Res 1978;42:661-675.

Colli-Franzone P, Guerri L, Tentoni S, Viganotti C, Baruffi S, Spaggiari S, Taccardi A mathematical procedure for solving the inverse problem of electrocardiography: analysis of the time-space accuracy from in vitro experimental data. Math Biosci 1985;77:353-396.

Durrer D, van Dam RT, Freud GE, Janse MJ, Meijler FL, Arzbaecher RC. Total excitation of the isolated human heart. Circulation 1970;41:899-912.

Spach MS and Barr RC. Ventricular intamural and epicardial potential distribution during ventricular activation and repolarization in the intact heart. Circ Res 1975;37:243-257.

Messinger-Rapport BJ, Rudy Y. Regularization of the inverse problem in electrocardiograpy: a model study. Math Biosci 1988;89:79-118.

Messinger-Rapport BJ, Rudy Y. Computational issues of importance to the inverse recovery of epicardial potentials in a realistic heart-torso geometry. Math Biosci 1989;97:85-120.

Tikhonov AN, Arsenin VY. Solutions of III-Posed Problems. Washington: V. H. Winston & Sons, 1977, pp. 27-94 (Missing pp. 28-94).

Colli-Franzone P, Guerri L, Taccardi B, Viganotti C. Finite element approximation of regularized solutions of the inverse potential problem of electrocardiography and applications to experimental data. Calcolo 1985;22:91-186.

Messinger-Rapport BJ, Rudy Y. Noninvasive recovery of epicardial potentials in a realistic heart-torso geometry. Normal sinus rhythm. Circ Res 1990;66:1023-1039.

Gulrajani RM. The forward and inverse problems of electrocardiography. IEEE Eng Med Biol 1998;17(5):84-122.

MacLeod RS, Brooks DH. Recent progress in inverse problems in electrocardiology. IEEE Eng Med Biol 1998;17(1):73-83.

Iakovidis I and Gulrajani RM. Improving Tikhonov regularization with linearly constrained optimization: application to the inverse epicardial potential solution. Math Biosci 1992;112:55-80.

Oster HS, Rudy Y. Regional regularization of the electrocardiographic inverse problem: a model study using spherical geometry. IEEE Trans Biomed Eng 1997;44:188-199.

Oster HS, Rudy Y. The use of temporal information in the regularization of the inverse problem of electrocardiography. IEEE Trans Biomed Eng 1992;39:65-75.

Greensite F and Huiskamp G. An improved method for estimating epicardial potentials from the body surface. IEEE Trans Biomed Eng 1998;45:98-104.

Khoury DS, Rudy Y. A model study of volume conductor effects on endocardial and intracavitary potentials. Circ Res 1992;71:511-525.

Khoury DS. Recovery of endocardial potentials from intracavitary potential data [Dissertation]. Cleveland, Ohio: Case Western Reserve University, 1993, pp. ii and iii.

Khoury DS, Rudy Y. Reconstruction of endocardial potentials from intracavitary probe potentials. A model study. Proc Comput Cardiol 1992, pp. 9-12.

Khoury DS. Use of current density in the regularization of the inverse problem of electrocardiology. Proc 16th IEEE/EMBS 1994, pp. 133-134.

Khoury DS, Marks GF. Adaptive regularization of the inverse problem in electrocardiography. Proc 17th IEEE/EMBS 1995.

Khoury DS, Taccardi B, Lux RL, Ershler PR, Rudy Y. Reconstruction of endocardial potentials and excitation sequences from intracavitary probe measurements. Localization of pacing sites and effects of myocardial structure. Circulation 1995;91:845-863.

Khoury DS, Berrier KL, Badruddin SM, Zoghbi WA. Three-dimensional electrophysiologic imaging of the intact dog left ventricle using a noncontact multielectrode cavitary probe. Study of sinus, paced, and spontaneous problem beats. Circulation 1998;97:399-409.

Velipasaoglu EO, Sun. H, Berrier KL, Khoury DS. Spatial regularization of the electrocardiographic inverse problem and its application to endocardial mapping. IEEE Trans Biomed Eng 2000;47:327-337.

Sun H, Velipasaoglu EO, Berrier KL, Khoury DS. Electrophysiological imaging of the right atrium using a noncontact multielectrode cavitary probe: study of normal and abnormal rhythms. PACE 1998;21[Pt. II]:2500-2505.

Rao L, Sun H, Khoury DS. Global Comparisons between contact and noncontact mapping techniques in the right atrium: role of cavitary probe size. Submitted to Ann Biomed Eng.

Velipasaoglu EO, Berrier KL, Sun H, Khoury DS. Determining locations of intracardiac basket and probe electrodes from multiplane fluoroscopic images. Proc Comput Cardiol 1998;25:465-468.

Velipasaoglu EO, Sun H, Khoury DS. Reconstruction of endocardial multielectrode basket geometry from multiplane fluoroscopic images. Proc 1st Joint Mtg BMES and EMBS. Atlanta, GA, 1999;276.

Schilling RJ, Peters NS, Davies DW. Feasibility of a noncontact catheter for endocardial mapping of human ventricular tachycardia. Circulation 1999;99:2543-2552.

Brebbia CA, Dominguez J. Boundary Elements. An Introductory Course. Southampton and Boston: Computational Mechanics Publications, 1989, chapter 2, p. 1.

Macchi E, Arisi G, Taccardi B. Intracavitary mapping: an improved method for locating the site of origin of ectopic ventricular beats by means of a mathematical model. Proc 10th IEEE/EMBS 1998, pp. 187-188.

Ren JF, Schwartzman D, Callans DJ, Brode SE, Gottlieb CD, Marchlinski FE. Intracardiac echocardiography (9 MHz) in humans: methods, imaging views and clinical utility. Ultrosound Med Biol 1999;25:1077-1086.

Ladd ME, Quick HH, Debatin JF, Interventional MRI and intravascular imaging. J Magn Reson Imaging 2000;12:534-546.

Khoury DS, Sun H, Velipasaoglu EO, Dupree D, McMillan A, Panescu D. Four-dimensional, biatrial mapping in the intact beating heart [Abstract]. PACE 2000;23:790.

Tikhonov AN, Arsenin VY. Solutions of Ill-Posed Problems. Washington: V. H. Winston & Sons, pp. 27-94, 1977.

Walcott GP, Reek S, Klein HU, Smith WM, Ideker RE. Cardiac mapping systems and their use in treating tachyarrhythmias. In Singer I, Barold SS, and Camm AJ (Eds): Nonpharmacological Therapy of Arrhythmias for the 21st Century: The State of the Art. Armonk, NY: Futura Publishing Co, pp. 591-606, 1998.

* cited by examiner

CARDIAC CATHETER IMAGING SYSTEM

CROSS-REFERENCE TO RELATED APPLICATIONS

This application claims the benefit of U.S. Provisional Application No. 60/325,707, filed Sep. 28, 2001.

STATEMENT REGARDING FEDERALLY SPONSORED RESEARCH OR DEVELOPMENT

Not Applicable.

REFERENCE TO A "SEQUENTIAL LISTING," A TABLE, OR A COMPUTER PROGRAM LISTING APPENDIX SUBMITTED ON A COMPACT DISC

Not Applicable.

BACKGROUND OF THE INVENTION

1. Field of the Invention

The invention involves catheters usable in medical evaluations of a condition of a living body, and more particularly, catheters that can detect based on electric, ultrasonic, or other types of sensing methods.

2. Description of Related Art

The related art can be reviewed via published patent applications, issued patents, and scholarly articles published in various medical and scientific journals. First, the following are the published applications and issued patents.

Published Patent Applications

The full disclosures of the following published patent applications are all incorporated herein by this reference:

20010021841 Title: "Automated longitudinal position translator for ultrasonic imaging probes, and methods of using same"

This discloses a longitudinal position translator that includes a probe drive module and a linear translation module. The probe drive module is coupled operatively to an ultrasonic imaging probe assembly having a distally located ultrasound transducer subassembly in such a manner that longitudinal shifting of the transducer subassembly may be effected.

20010021811 Title: "Method and apparatus for intravascular two-dimensional ultrasonography"

This discloses a catheter for insertion in the blood vessel of a patient for ultrasonically imaging the vessel wall. The catheter includes a tubular element and an internally housed drive cable for effective circumferential scan about the catheter of an ultrasonic generating means.

20010021805 Title: "Method and apparatus using shaped field of repositionable magnet to guide implant"

This discloses methods and apparatuses for displaying and using a shaped field of a repositionable magnet to move, guide, and/or steer a magnetic seed or catheter in living tissue for medicinal purposes.

20010020149 Title: "Safety mechanism and methods to prevent rotating imaging device from exiting a catheter"

This discloses systems and methods to prevent rotation of an imaging device if the imaging device is advanced beyond a distal end of a catheter.

20010020126 Title: "Systems And Methods For Visualizing Tissue During Diagnostic Or Therapeutic Procedures"

This discloses a catheter tube that carries an imaging element for visualizing tissue. The catheter tube also carries a support structure, which extends beyond the imaging element for contacting surrounding tissue away from the imaging element. The support element stabilizes the imaging element, while the imaging element visualizes tissue in the interior body region. The support structure also carries a diagnostic or therapeutic component to contact surrounding tissue.

20010016687 Title: "Ultrasound imaging guidewire with static central core and tip"

This discloses an ultrasound imaging guidewire, that is inserted into a patient's body. The guidewire has a static central core and an imaging guidewire body comprising an acoustical scanning device. The acoustical scanning device can be rotated to obtain 360 degree acoustical images of a site of interest in the patient's body.

20010011889 Title: "Magnetic resonance imaging device"

This discloses an imaging probe having all components necessary to allow magnetic resonance measurements and imaging of local surroundings of the probe.

20010009976 Title: "Systems for recording use of structures deployed in association with heart tissue"

This discloses an image controller that generates an image of a structure while in use with heart tissue in a patient.

20010007940 Title: "Medical device having ultrasound imaging and therapeutic means"

This discloses an ultrasound transducer for ultrasound imaging, RF thermal therapy, cryogenic therapy and temperature sensing, for treating a tissue or lesion.

Issued Patents

The full disclosures of the following patents are all incorporated herein by this reference:

U.S. Pat. No. 6,283,920 Ultrasound transducer assembly
U.S. Pat. No. 6,277,077 Catheter including ultrasound transducer with emissions attenuation
U.S. Pat. No. 6,267,727 Methods and apparatus for non-uniform rotation distortion detection in an intravascular ultrasound imaging system
U.S. Pat. No. 6,266,564 Method and device for electronically controlling the beating of a heart
U.S. Pat. No. 6,263,229 Miniature magnetic resonance catheter coils and related methods
U.S. Pat. No. 6,251,078 Preamplifier and protection circuit for an ultrasound catheter
U.S. Pat. No. 6,246,899 Ultrasound locating system having ablation capabilities
U.S. Pat. No. 6,233,477 Catheter system having controllable ultrasound locating means
U.S. Pat. No. 6,216,026 Method of navigating a magnetic object, and MR device
U.S. Pat. No. 6,210,356 Ultrasound assembly for use with a catheter
U.S. Pat. No. 6,200,269 Forward-scanning ultrasound catheter probe
U.S. Pat. No. 6,192,144 MR method for the image-assisted monitoring of the displacement of an object, and MR device for carry out the method
U.S. Pat. No. 6,178,346 Infrared endoscopic imaging in a liquid with suspended particles: method and apparatus
U.S. Pat. No. 6,173,205 Electrophysiology catheter
U.S. Pat. No. 6,165,127 Acoustic imaging catheter and the like
U.S. Pat. No. 6,162,179 Loop imaging catheter
U.S. Pat. No. 6,152,878 Intravascular ultrasound enhanced image and signal processing U.S. Pat. No. 6,149,598 Ultrasound endoscope
U.S. Pat. No. 6,149,596 Ultrasonic catheter apparatus and method
U.S. Pat. No. 6,240,307 Endocardial mapping system
U.S. Pat. No. 5,662,108 Electrophysiology mapping system
U.S. Pat. No. 5,713,946 Apparatus and method for intrabody mapping
U.S. Pat. No. 5,546,951 Method and apparatus for studying cardiac arrhythmias
U.S. Pat. No. 5,480,422 Apparatus for treating cardiac arrhythmias
U.S. Pat. No. 6,277,077 Catheter including ultrasound transducer with emissions attenuation
U.S. Pat. No. 6,216,027 System for electrode localization using ultrasound
U.S. Pat. No. 6,014,579 Endocardial mapping catheter with movable electrode
U.S. Pat. No. 6,443,894 Medical diagnostic ultrasound system and method for mapping surface data for three dimensional imaging The following related art comes from scholarly articles published in various medical and scientific journals. The numbers in brackets refer to the reference numbers listed at the end of the specification.

Heart rhythm disorders (atrial and ventricular arrhythmias) result in significant morbidity and mortality. Atrial fibrillation is the most common cardiac arrhythmia: it affects more than two million Americans, is responsible for one-third of all strokes over the age of 65 years, and annually costs 9 billion dollars to manage [1]. Furthermore, about 300,000 Americans die of sudden cardiac death annually, primarily due to ventricular tachyarrhythmias (ventricular tachycardia and fibrillation) which result in intractable, extremely rapid heartbeats [2]. Unfortunately, current pharmacological therapy for managing cardiac arrhythmias is often ineffective and, at times, can cause arrhythmias [3,4], thereby shifting emphasis to nonpharmacological therapy (such as ablation, pacing, and defibrillation) [5–8]. Catheter ablation has been successful in managing many atrial and a few ventricular tachyarrhythmias [9]. However, due to limitations in present mapping techniques, brief, chaotic, or complex arrhythmias such as atrial fibrillation and ventricular tachycardia cannot be mapped adequately, resulting in unsuccessful elimination of the arrhythmia. In addition, localizing abnormal beats and delivering and quantifying the effects of therapy such as ablation are very time consuming. Selecting appropriate pharmacological therapies and advancing nonpharmacological methods to manage cardiac arrhythmias are contingent on developing mapping techniques that identify mechanisms of arrhythmias, localize their sites of origin with respect to underlying cardiac anatomy, and elucidate effects of therapy. Therefore, to successfully manage cardiac arrhythmias, electrical-anatomical imaging on a beat-by-beat basis, simultaneously, and at multiple sites is required.

Electrical mapping of the heartbeat, whereby multielectrode arrays are placed on the exterior surface of the heart (epicardium) to directly record the electrical activity, has been applied extensively in both animals and humans [10–13]. Although epicardial mapping provides detailed information on sites of origin and mechanisms of abnormal heart rhythms (arrhythmias), its clinical application has great limitation: it is performed at the expense of open-chest surgery. In addition, epicardial mapping does not provide access to interior heart structures that play critical roles in the initiation and maintenance of abnormal heartbeats.

Many heart rhythm abnormalities (arrhythmias) originate from interior heart tissues (endocardium). Further, because the endocardium is more safely accessible (without surgery) than the epicardium, most electrical mapping techniques and delivery of nonpharmacological therapies (e.g. pacing and catheter ablation) have focused on endocardial approaches. However, current endocardial mapping techniques have certain limitations. Traditional electrode-catheter mapping performed during electrophysiology procedures is confined to a limited number of recording sites, is time consuming, and is carried out over several heartbeats without accounting for possible beat-to-beat variability in activation [14]. While newly introduced catheter-mapping approaches provide important three-dimensional positions of a roving electrode-catheter through the use of "special" sensors, mapping is still performed over several heartbeats [15–17]. On the other hand, although multielectrode basket-catheters [18,19] measure endocardial electrical activities at multiple sites simultaneously by expanding the basket inside the heart so that the electrodes are in direct contact with the endocardium, the basket is limited to a fixed number of recording sites, may not be in contact with the entire endocardium, and may result in irritation of the myocardium.

An alternative mapping approach utilizes a noncontact, multielectrode cavitary probe [20] that measures electrical activities (electrograms) from inside the blood-filled heart cavity from multiple directions simultaneously. The probe electrodes are not necessarily in direct contact with the endocardium; consequently, noncontact sensing results in a smoothed electrical potential pattern [21]. Cavitary probe mapping was also conducted on experimental myocardial infarction [22]. More recently, nonsurgical insertion of a noncontact, multielectrode balloon-catheter, that does not occlude the blood-filled cavity, has been reported in humans [23]. This catheter was used to compute electrograms on an ellipsoid that approximated the endocardium.

Present mapping systems cannot provide true images of endocardial anatomy. Present systems often delineate anatomical features based on (1) extensive use of fluoroscopy; (2) deployment of multiple catheters, or roving the catheters, at multiple locations; and (3) assumptions about properties of recorded electrograms in relation to underlying anatomy (e.g. electrograms facing a valve are low in amplitude). However, direct correlation between endocardial activation and cardiac anatomy is important in order to clearly identify the anatomical sources of abnormal heartbeats, to understand the mechanisms of cardiac arrhythmias and their sequences of activation within or around complex anatomical structures, and to deliver appropriate therapy.

Early applications of the "inverse problem" of electrocardiography sought to noninvasively reconstruct (compute) epicardial surface potentials (electrograms) and activation sequences of the heartbeat based on noncontact potentials measured at multiple sites on the body surface [24,25]. The computed epicardial potentials were in turn used to delineate information on cardiac sources within the underlying myocardium [26,27]. To solve the "inverse problem", numeric techniques have been repeatedly tested on computer, animal, and human models [28–38]. Similarly, computing endocardial surface electrical potentials (electrograms) based on noncontact potentials (electrograms) measured with the use of a multielectrode cavitary probe constitutes a form of endocardial electrocardiographic "inverse problem."

The objective of the endocardial electrocardiographic "inverse problem" is to compute virtual endocardial surface electrograms based on noncontact cavitary electrograms measured by multielectrode probes. Preliminary studies have demonstrated that methods for acquisition of cavitary electrograms and computation of endocardial electrograms in the beating heart have been established and their accuracy globally confirmed [39–50]. Determining the probe-endocardium geometrical relationship (i.e. probe position and orientation with respect to the endocardial surface) is required to solve the "inverse problem" and a prerequisite for accurate noncontact electrical-anatomical imaging. In initial studies, fluoroscopic imaging provided a means for beat-by-beat global validation of computed endocardial activation in the intact, beating heart [46–50]. Furthermore, epicardial echocardiography [45] was used to determine the probe-cavity geometrical model. However, complex geometry, such as that of the atrium, may not be easily characterized by transthoracic or epicardial echocardiography.

Accurate three-dimensional positioning of electrode-catheters at abnormal electrogram or ablation sites on the endocardium and repositioning of the catheters at specific sites are important for the success of ablation. The disadvantages of routine fluoroscopy during catheterization include radiation effects and limited three-dimensional localization of the catheter. New catheter-systems achieve better three-dimensional positioning by (1) using a specialized magnetic sensor at the tip of the catheter that determines its location with respect to an externally applied magnetic field [15], (2) calculating the distances between a roving intracardiac catheter and a reference catheter, each carrying multiple ultrasonic transducers [16], (3) measuring the field strength at the catheter tip-electrode, while applying three orthogonal currents through the patient's body to locate the catheter [17]; and (4) emitting a low-current locator signal from the catheter tip and determining its distance from a multielectrode cavitary probe [51]. With these mapping techniques true three-dimensional imaging of important endocardial anatomical structures is not readily integrated (only semi-realistic geometric approximations of the endocardial surface), and assumptions must often be made about properties of recorded electrograms in relation to underlying anatomy (e.g. electrograms facing the tricuspid and mitral annuli are low in amplitude).

BRIEF SUMMARY OF THE INVENTION

A system and methods are described that make possible the combined use of (1) a lumen-catheter carrying a plurality of sensing electrodes (multielectrode catheter-probe) for taking multiple noncontact measurements from different directions of the electrical characteristics of interior tissue such as the heart (endocardium) and (2) an internal coaxial catheter carrying one or more imaging elements for visualizing the anatomical characteristics of the tissue. A middle, coaxial lumen-catheter (sheath) provides structural support and serves as a conduit for advancing or withdrawing the multielectrode catheter over its surface, or inserting the anatomical imaging catheter through its lumen. The imaging catheter is inserted inside the multielectrode catheter-probe (or the supporting lumen-catheter when in use) and is moved to detect the tissue from inside the lumen using different modalities such as ultrasound, infrared, and magnetic resonance. Both the electrical and anatomical measurements are sent to a data acquisition system that in turn provides combined electrical and anatomical graphical or numerical displays to the operator.

In another feature of the present invention, the catheter imaging system simultaneously maps multiple interior heart surface electrical activities (endocardial electrograms) on a beat-by-beat basis and combines three-dimensional activation-recovery sequences with endocardial anatomy. Electrical-anatomical imaging of the heart, based on (1) cavitary electrograms that are measured with a noncontact, multielectrode probe and (2) three-dimensional endocardial anatomy that is determined with an integrated anatomical imaging modality (such as intracardiac echocardiography), provides an effective and efficient means to diagnose abnormal heartbeats and deliver therapy.

In another feature of the present invention, the integrated electrical-anatomical imaging catheter system contains both a multielectrode probe and an anatomical imaging catheter, which can be percutaneously introduced into the heart in ways similar to standard catheters used in routine procedures. This "noncontact" imaging approach reconstructs endocardial surface electrograms from measured probe electrograms, provides three-dimensional images of cardiac anatomy, and integrates the electrical and anatomical images to produce three-dimensional isopotential and isochronal images.

In another feature of the present invention, the method improves the understanding of the mechanisms of initiation, maintenance, and termination of abnormal heartbeats, which could lead to selecting or developing better pharmacological or nonpharmacological therapies. Mapping is conducted with little use of fluoroscopy on a beat-by-beat basis, and allows the study of brief, rare, or even chaotic rhythm disorders that are difficult to manage with existing techniques.

In another feature of the present invention, there is a means to navigate standard diagnostic-therapeutic catheters, and accurately guide them to regions of interest within an anatomically-realistic model of the heart that is derived from ultrasound, infrared, or magnetic resonance. The present invention provides considerable advantages in guiding clinical, interventional electrophysiology procedures, such as imaging anatomical structures, confirming electrode-tissue contact, monitoring ablation lesions, and providing hemodynamic assessment.

DETAILED DESCRIPTION OF THE INVENTION

Figure 1:
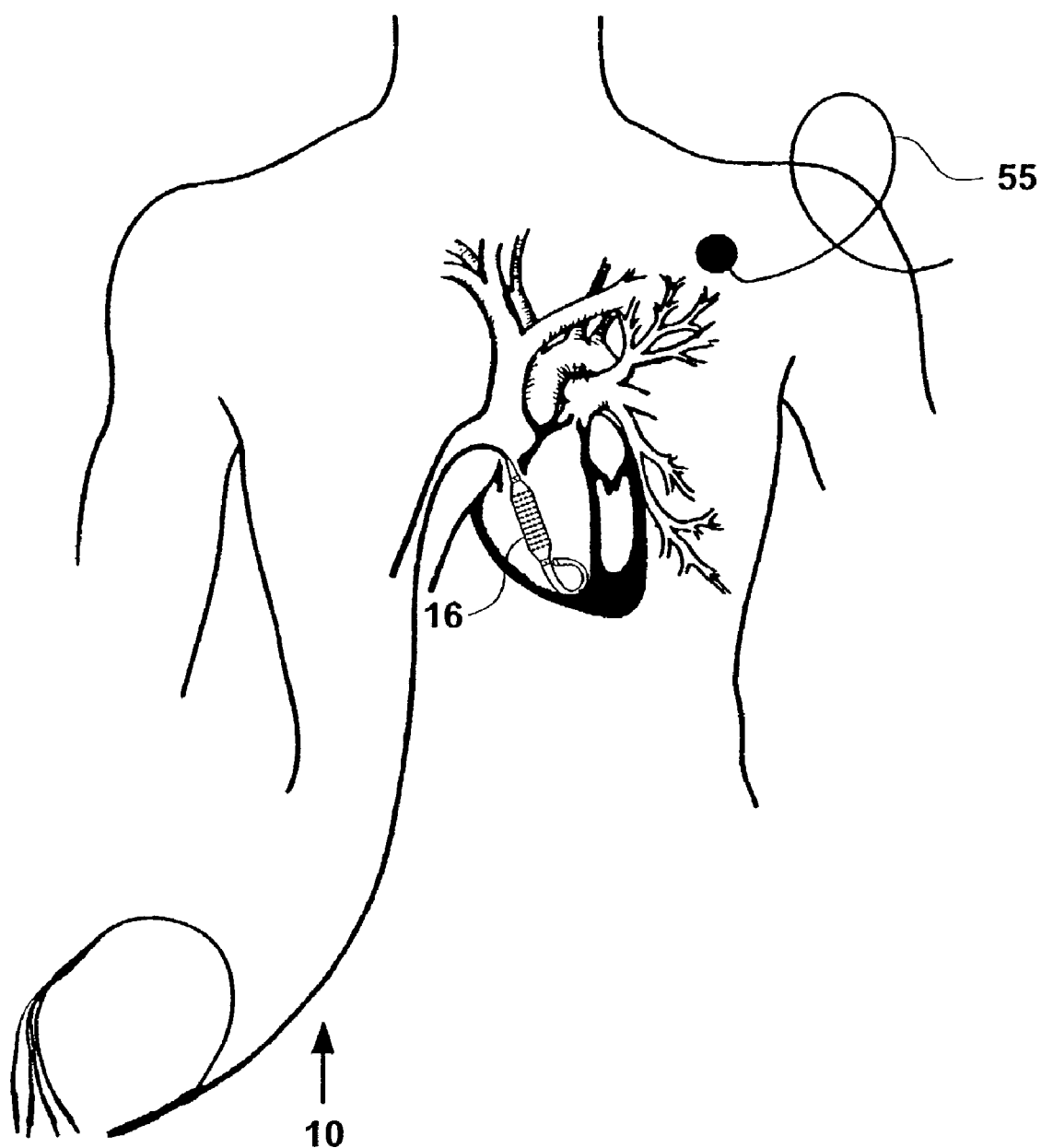
FIG. 1 illustrates the system of the present invention in use with a human patient.

FIG. 1 illustrates an electrical-anatomical imaging catheter-system 10 in use in a human patient. The catheter is percutaneously inserted through a blood vessel (vein or artery) and advanced into the heart cavity. The catheter detects both electrical and anatomical properties of interior heart tissue (endocardium).

Figure 2:
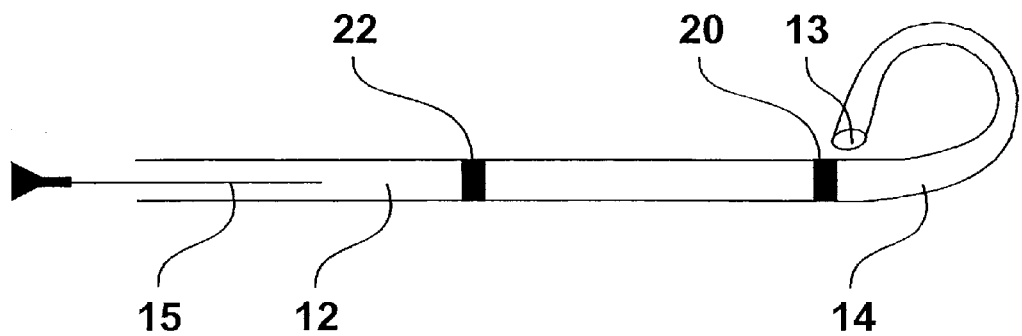
FIG. 2 illustrates a lumen sheath with a pig-tail at its distal end and a guide wire inside its lumen.

Referring now to FIG. 2, the electrical-anatomical imaging catheter-system 10 includes a lumen sheath 12 (about 3 mm in diameter) which has a pig tail distal end 14 to minimize motion artifacts inside the heart cavity. A guide wire 15 is advanced to a tip 13 to guide the sheath 12. The sheath 12 provides structural support for a coaxial multi-electrode catheter-probe 16 (illustrated in FIG. 3A and FIG. 3B) that slides over the surface of the sheath 12, and records noncontact cavitary electrical signals (electrograms) from multiple directions. The sheath 12 also functions as a conduit for inserting an anatomical imaging catheter 18 (illustrated in FIG. 4) such as a standard intracardiac echocardiography (ICE) catheter that records continuous echocardiographic images of the heart interior. With this approach, the sheath 12 maintains the same imaging axis and direction over several deployments inside the heart cavity of both the probe 16 and the anatomical imaging catheter 18. Radiopaque and sonopaque ring marker 20 at the distal end of the sheath 12 and radiopaque and sonopaque ring marker 22 at the proximal end of the sheath 12 aid in verifying the probe 16 and the anatomical imaging catheter 18 locations.

Figure 3A:
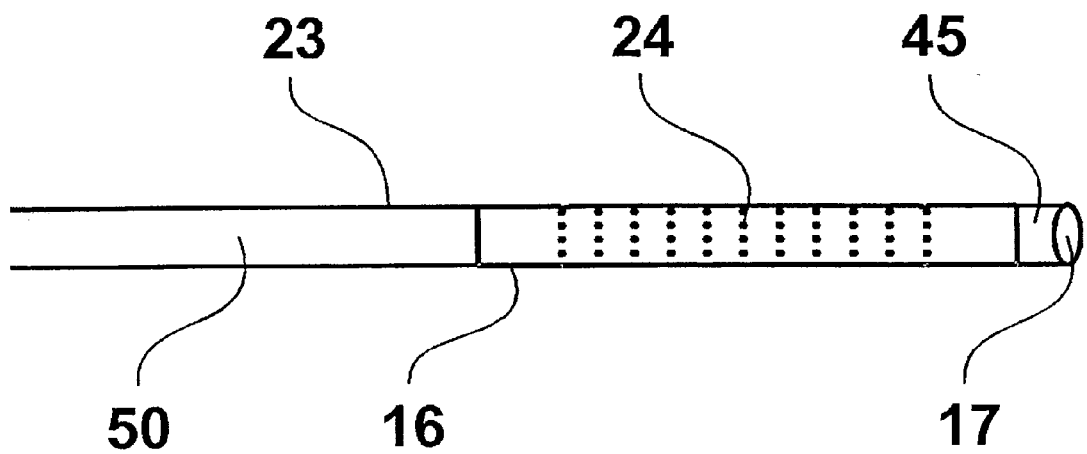
FIG. 3A illustrates a multielectrode catheter-probe with a lumen inside its shaft.

Referring now to FIG. 3A, the electrical-anatomical imaging catheter-system 10 includes a lumen catheter which carries a plurality of sensing electrodes 24 on its surface that make up the multielectrode probe 16. The electrodes 24 are arranged in columns. The diameter of the probe 16 is similar to that of shaft 23 of the probe 16 (on the order of 3 mm). The sheath 12 and the anatomical imaging catheter 18 both coaxially fit inside the lumen of the probe 16. The catheter-probe 16 has a straight distal end 45 that permits sliding the probe 16 over the coaxial lumen sheath 12. In this state the probe 16 is easily inserted percutaneously by the operator through a blood vessel and advanced into the heart cavity. By sliding the catheter-probe 16 over the central sheath 12, it is possible to place the probe 16 along the axis of the cavity. The shaft 23 of the probe 16 is shorter than the central sheath 12 so that it slides easily over the sheath 12 in and out of the heart cavity.

Figure 3B:
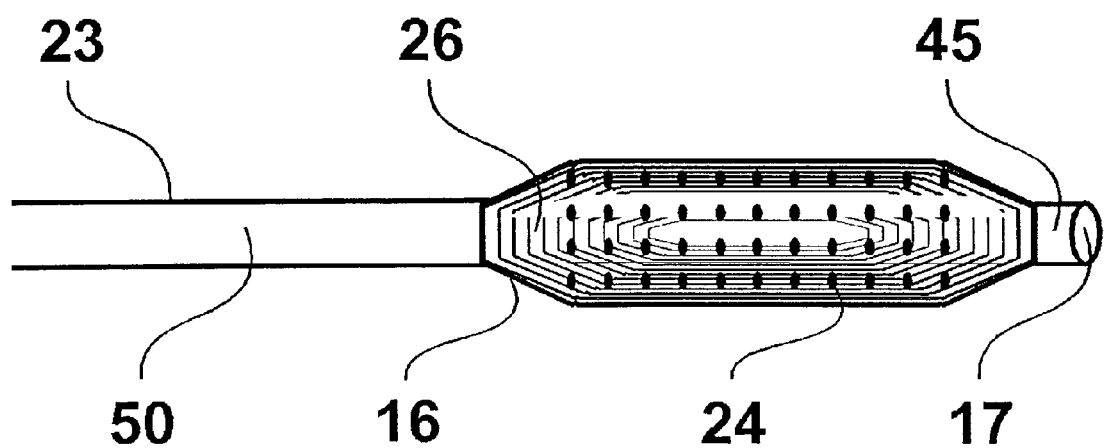
FIG. 3B illustrates an alternative embodiment of a multielectrode lumen catheter-probe whereby a grid of electrodes can be expanded.

FIG. 3B illustrates another embodiment of part of the electrical-anatomical imaging catheter-system 10 of the present invention, in which for the probe 16, the electrodes 24 are laid on a central balloon 26 that is inflated to a fixed diameter without the electrodes 24 necessarily touching the interior surface of the heart. The balloon is similar to angioplasty catheters used in routine catheterization procedures. The balloon 26 is inflated inside the heart cavity to enlarge the probe 16. The sheath 12 and the anatomical imaging catheter 18 (illustrated in FIG. 4) fit inside the lumen 50. The probe 16 has a straight distal end 45 that permits sliding the probe 16 over the coaxial lumen sheath 12. By sliding the probe 16 over the central sheath 12, it is possible to place the probe 16 along the axis of the heart cavity. In its collapsed state the size of the probe 16 is similar to that of the sheath 12. Thus, the operator is able to insert the probe percutaneously and inflate it inside the heart without occluding the cavity. The shaft 23 of the probe 16 is shorter than the central sheath 12 so that the probe 16 slides easily over the sheath 12 in and out of the cavity.

Figure 3C:
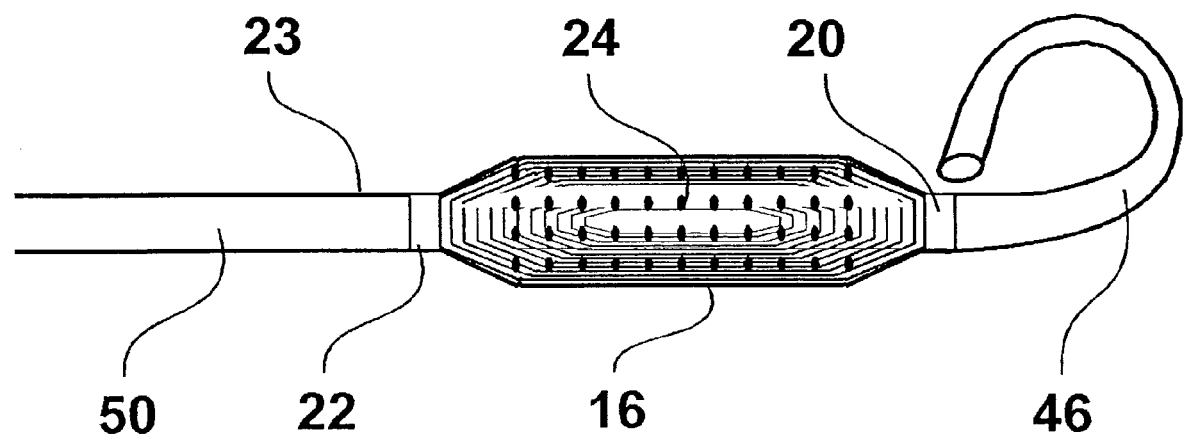
FIG. 3C illustrates an alternative embodiment of a multielectrode lumen catheter-probe with a pig-tail at its distal end for structural support.

In another embodiment of the electrical-anatomical imaging catheter-system 10, FIG. 3C illustrates the probe 16 with a pig-tail 46 at its distal end to minimize motion artifacts of the probe 16. In this embodiment, the probe 16 is used independently of the lumen sheath 12. The anatomical imaging catheter 18 (illustrated in FIG. 4) fits inside the lumen of the probe 16.

Figure 4:
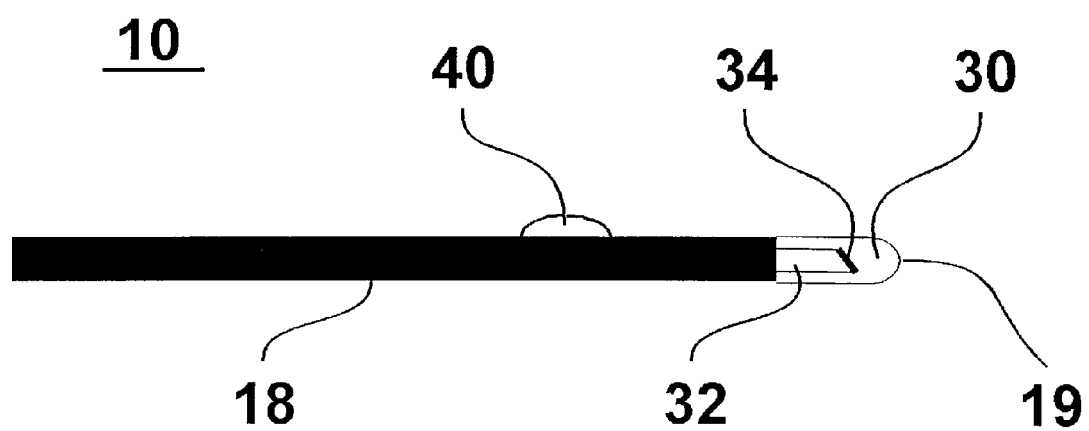
FIG. 4 illustrates an anatomical imaging catheter such as intracardiac echocardiography catheter.

Referring now to FIG. 4, the anatomical imaging catheter 18 is used to image interior structures of the heart. In the preferred embodiment, the catheter 18 is a 9-MHz intracardiac echocardiography catheter (Model Ultra ICE, manufactured by Boston Scientific/EPT, located in San Jose, Calif.). To acquire echocardiographic images, the catheter 18 connects to an imaging console (Model ClearView, manufactured by Boston Scientific/EPT, located in San Jose, Calif.). The catheter 18 has a distal imaging window 30 and a rotatable imaging core 32 with a distal transducer 34 that emits and receives ultrasound energy. Continuous rotation of the transducer provides tomographic sections of the heart cavity. The design of the present invention allows for integrating other anatomical imaging catheters presently under development such as echocardiography catheters carrying multiple phased-array transducers, infrared, and magnetic resonance imaging catheters. While the anatomical imaging catheter 18 is in use, the three-dimensional anatomical reconstruction assumes that the catheter 18 is straight and thus straightens the image of the heart cavity. If the catheter 18 curves, the image is distorted, or, if the catheter 18 rotates during pullback, the image is twisted. Therefore, in the preferred embodiment, a position and orientation sensor 40 is added to the catheter 18.

Figure 5A:
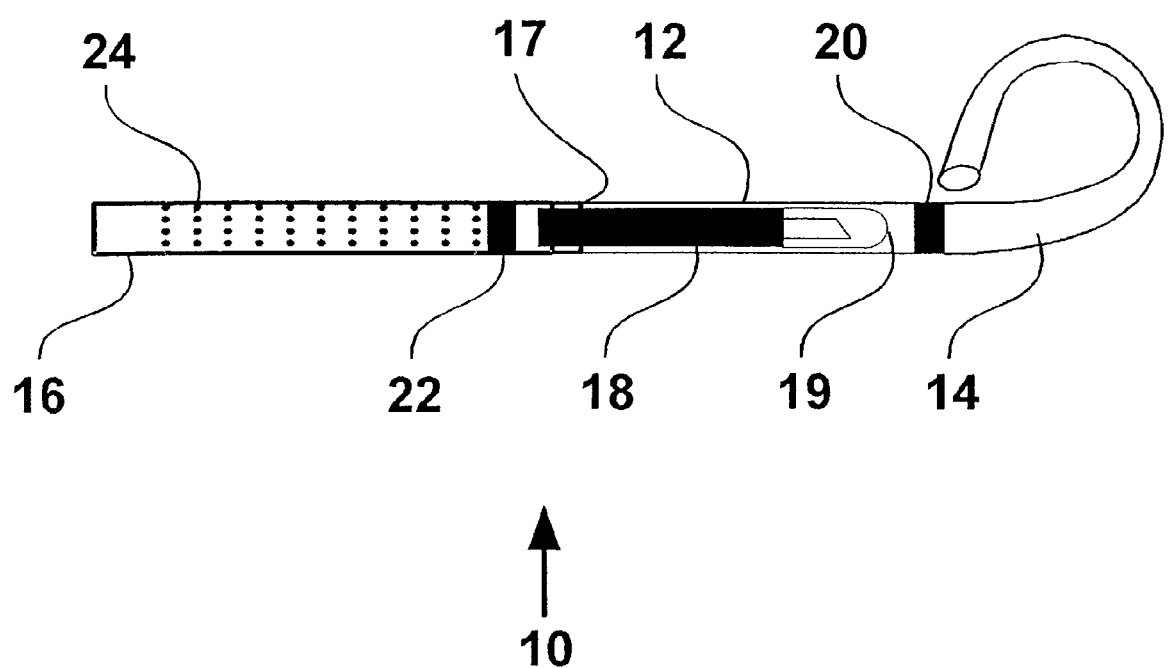
FIG. 5A illustrates a configuration that combines the sheath (of FIG. 2) with the multielectrode catheter-probe (of FIG. 3A) over its surface at the proximal end and the anatomical imaging catheter (of FIG. 4) advanced inside the lumen at the distal end.

Referring now to FIG. 5A, an integrated, noncontact, electrical-anatomical imaging catheter-system 10 is illustrated that combines the sheath 12 with the multielectrode catheter-probe 16 over its surface at the proximal end, and the anatomical imaging catheter 18 inside the lumen at the distal end. In operation, the probe 16 is preloaded over the central sheath 12, thereby enabling the probe 16 to move in and out of the heart cavity in small increments over a fixed axis. The guide wire 15 is placed inside the central sheath 12 to ensure the pig-tail end 14 remains straight during insertion through a blood vessel. With the probe 16 loaded on the sheath 12 and pulled back, the sheath 12 is advanced through a blood vessel and placed inside the heart cavity under the guidance of fluoroscopy, and the guide wire 15 is then removed. The anatomical imaging catheter 18 is then inserted through the lumen of the central sheath 12, replacing the guide wire 15, and advanced until a tip 19 of the catheter 18 is situated at the pre-determined radiopaque and sonopaque distal marker 20 on the sheath 12. The catheter 18 is pulled back from the distal marker 20 to the proximal marker 22 on the sheath 12 at fixed intervals, and noncontact anatomical images are continuously acquired at each interval.

Figure 5B:
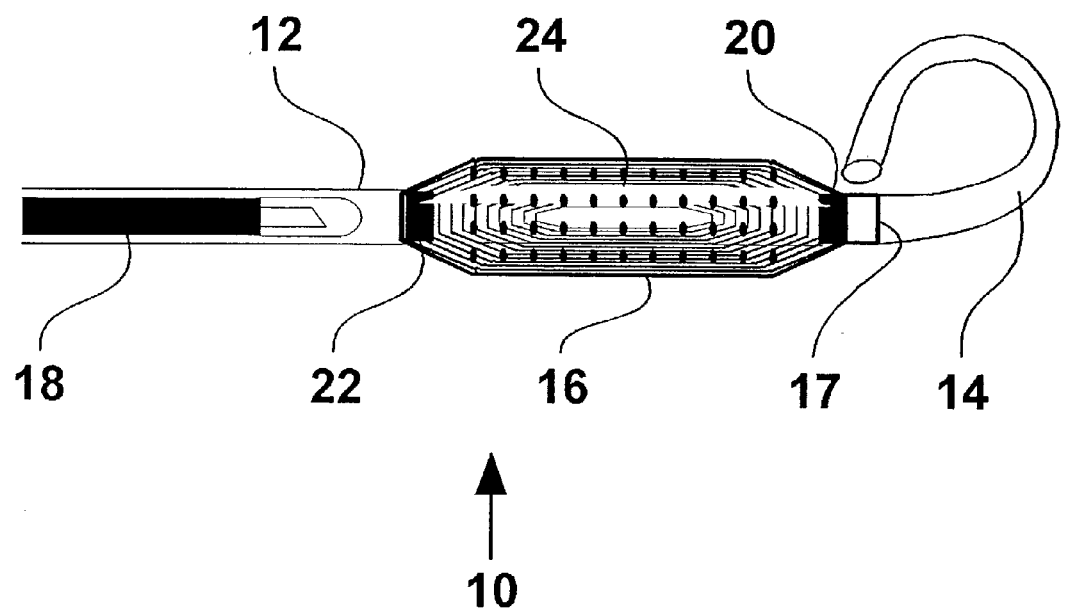
FIG. 5B illustrates an alternative embodiment that combines the sheath (of FIG. 2) with the multielectrode catheter-probe (of FIG. 3B) advanced over its surface to the distal end and the anatomical imaging catheter (of FIG. 4) inside the lumen at the proximal end.

Referring now to FIG. 5B, under the guidance of fluoroscopy, the probe 16 is advanced over the central sheath 12 until a tip 17 is at the distal marker 20, and the balloon 26 (if used) is inflated to unfold the probe 16. The probe 16 then simultaneously acquires noncontact cavitary electrograms.

Figure 6:
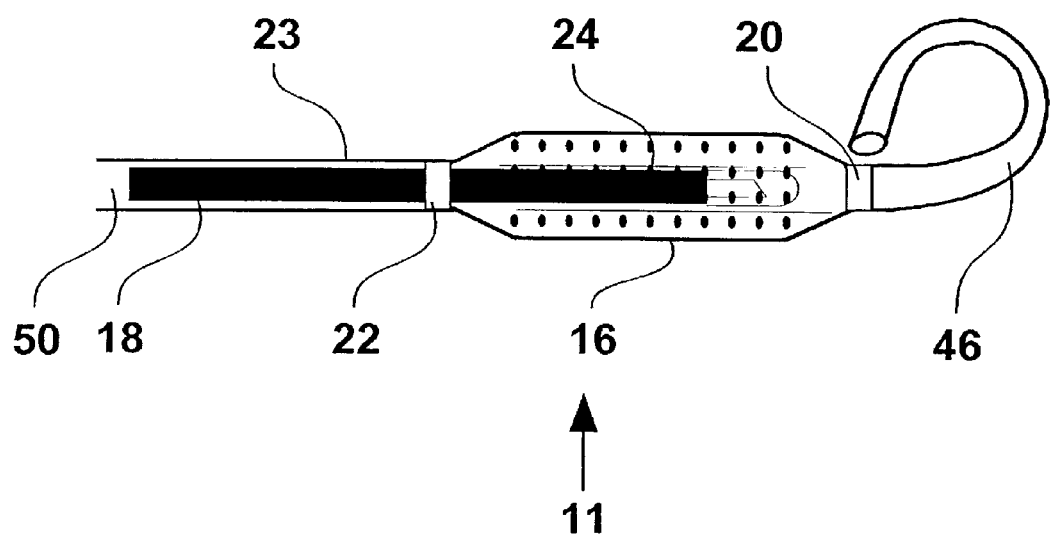
FIG. 6 illustrates an alternative embodiment that combines the multielectrode catheter-probe (of FIG. 3C) with the anatomical imaging catheter (of FIG. 4) inside its lumen.

Referring now to FIG. 6, an alternate embodiment of the integrated electrical-anatomical imaging catheter system 10 is illustrated, labeled as an integrated electrical-anatomical imaging catheter system 11, in which the lumen sheath 12 is eliminated. A multielectrode lumen catheter-probe 16 with a pig-tail 46 at its distal end is inserted inside the heart cavity and is used to acquire noncontact electrograms. The anatomical imaging catheter 18 is inserted inside the lumen of the catheter-probe 16, and imaging is performed from inside the probe 16.

Unipolar cavitary electrograms sensed by the noncontact multielectrode probe 16 with respect to an external reference electrode 55 (shown in FIG. 1) along with body surface electrocardiogram signals, are simultaneously acquired with a computer-based multichannel data acquisition mapping system, which, in the preferred embodiment, is the one built by Prucka Engineering-GE Medical Systems, located in Milwaukee, Wis. The mapping system amplifies and displays the signals at a 1 ms sampling interval per channel. The mapping system displays graphical isopotential and isochronal maps that enable evaluation of the quality of the data acquired during the procedure and interaction with the study conditions. The multiple anatomical images (such as ICE) are digitized, and the interior heart borders automatically delineated. The cavity three-dimensional geometry is rendered in a virtual reality environment, as this advances diagnostic and therapeutic procedures.

To reconstruct the electrical activities (electrical potentials, V) on the interior heart surface (endocardium) based on electrical information measured by the cavitary multielectrode probe 16 and anatomical information derived from the anatomical imaging catheter 18, Laplace's equation ($\nabla^2 V=0$) is numerically solved in the blood-filled cavity between the probe 16 and the endocardium (similar to previous studies [40–50]). The boundary element method is employed in computing the electrical potentials in a three-dimensional geometry [52]. A numeric regularization technique (filtering) based on the commonly used Tikhonov method [30] is employed to find the electrical potentials on the endocardium. Here, the electrical potentials are uniquely reconstructed on the real endocardial anatomy derived from the anatomical imaging catheter 18.

Nonfluoroscopic three-dimensional positioning and visualization of standard navigational electrode-catheters is clinically necessary for (1) detailed and localized point-by-point mapping at select interior heart regions, (2) delivering nonpharmacological therapy such as pacing or ablation, (3) repositioning the catheters at specific sites, and (4) reducing the radiation effects of fluoroscopy during catheterization. To guide three-dimensional positioning and navigation of standard electrode-catheters, a low-amplitude location electrical signal is emitted between the catheter tip-electrode and the external reference electrode 55, and sensed by multiple electrodes 24 on the surface of the probe 16. Similar to previous work [53], the catheter tip is localized by finding the x, y, and z coordinates of a location point p. The location of the emitting electrode is determined by minimizing $[F(p)-V(p)]^T[F(p)-V(p)]$ with respect to p, where V(p) are the electrical potentials measured on the probe 16, and F(p) are the electrical potentials computed on the probe 16 using an analytical (known) function and assuming an infinite, homogeneous conducting medium. This process also constructs the shape of the catheter within the cavity by determining the locations of all catheter electrodes. Alternatively, the location and shape of the roving electrode-catheter is determined with respect to the underlying real anatomy by direct visualization with the anatomical imaging catheter 18.

The method of the present invention senses the location signal by multiple probe electrodes 24 simultaneously, thereby localizing the roving catheter more accurately than prior art methods. Furthermore, the method of the present invention reconstructs the shape of the roving catheter during navigation by emitting a location signal from each of the catheter electrodes and determining their locations within the cavity. With this approach, online navigation of standard electrode-catheters is performed and displayed within an anatomically-correct geometry derived from ultrasound, infrared, or magnetic resonance, and without extensive use of fluoroscopy.

LITERATURE CITED

1. Benjamin E J, Wolf P A, Agostino R B, Silbershatz H, Kannel W B, Levy D. Impact of atrial fibrillation on the risk of death: the Framingham Heart Study. Circulation 1998;98:946–952.
2. Zipes D P and Wellens H J J. Sudden cardiac death. Circulation 1998;98:2334–2351.
3. The Cardiac Arrhythmia Suppression Trial (CAST) Investigators. Effect of encainide and flecainide on mortality in a randomized trial of arrhythmia suppression after myocardial infarction. N Engl J Med 1989;321:406–412.
4. The ESVEM Investigators. Determinants of predicted efficacy of antiarrhythmic drugs in the electrophysiologic study versus electrocardiographic monitoring trial. Circulation 1993;87:323–329.
5. Jackman W M, Beckman K J, McClelland J H, Wang X, Friday K J, Roman C A, Moulton K P, Twidale N, Hazlitt A, Prior M I, Oren J, Overholt E D, Lazzarra R. Treatment of supraventricular tachycardia due to atrioventricular nodal reentry by radiofrequency catheter ablation of slow-pathway conduction. N Engl J Med 1992;327:313–318.
6. Calkins H, Yong P, Miller J M, Olshansky B, Carlson M, Saul P, Huang S K S, Liem B, Klein L S, Moser S A, Bloch D A, Gillette P, Prystowsky E, for the Atakr Multicenter Investigators Group. Catheter ablation of accessory pathways, atrioventricular nodal reentrant tachycardia, and the atrioventricular junction: final results of a prospective, multicenter clinical trail. Circulation 1999;99:262–270.
7. Papageorgiou P, Anselme F, Kirchlof C J H J, Monahan K, Rasmussen C A F, Epstein L M, Josephson M E. Coronary sinus pacing prevents induction of atrial fibrillation. Circulation 1997;96:1893–1898.
8. Moss A J, Hall J, Cannom D S, Daubert J P, Higgins S L, Klein H, Levine J L, Saksena S, Waldo A L, Wilber D, Brown M W, Heo M, for the Multicenter Automatic Defibrillator Implantation Trial Investigators. Improved survival with an implanted defibrillator in patients with coronary disease at high risk for ventricular arrhythmia. N Engl J Med 1996;335:1933–40.
9. Zhu W X, Maloney J D, Pinski S, Nitta J, Fitzgerald D M, Trohman R G, Khoury D S, Saliba W, Belco K M, Rizo-Patron C, Simmons T W. Efficacy and safety of radiofrequency catheter ablation of symptomatic ventricular ectopy. J Am Coll Cardiol 1995;26:843–849.
10. Waldo A L, Vitikainen K J, Hoffman B F. The sequence of retrograde atrial activation in the canine heart. Circ Res 1975;37:156–163.
11. Walcott G P, Reek S, Klein H U, Smith W M, Ideker R E. Cardiac mapping systems and their use in treating tachyarrhythmias. In Singer I, Barold S S, and Camm A J (Eds): Nonpharmacological Therapy of Arrhythmias for the 21st Century: The State of the Art. Armonk, N.Y.: Futura Publishing Co, 1998, pp 591–606.
12. Chen P S, Moser Km, Dembitsky W P, Auger W R, Daily P O, Calisi C M, Jamieson S W, Feld G K. Epicardial activation and repolarization patterns in patients with right ventricular hypertrophy. Circulation 1991;83:104–118.

13. Konings K T S, Smeets J L R M, Penn O C, Wellens H J J, Allessie M A. Configuration of unipolar atrial electrograms during electrical induced atrial fibrillation in humans. Circulation 1997;95:1231–1241.

14. Josephsen M E, Horowitz L N, Spielman S R, Waxman H L, Greespan A M. Role of catheter mapping in the preoperative evaluation of ventricular tachycardia. Am J Cardiol 1982;49:207–220.

15. Gepstein L, Hayam G, Ben-Haim S A. A novel method for nonfluoroscopic catheter-based electroanatomical mapping of the heart. In vitro and in vivo accuracy results. Circulation 1997;95:1611–1622.

16. De Groot N M S, Bootsma M, Van Der Velde E T, Schalij M J. Three-dimensional catheter positioning during radiofrequency ablation in patients: first application of a real-time position management system. J Cardiovasc Electrophysiol 2000;11:1183–1192.

17. Wittkampf F H M, Wever E F D, Derksen R, Wilde A A M, Ramanna H, Hauer R N W, Robles de Medlina E O. LocaLisa. New technique for real-time 3-dimensional localization of regular intracardiac electrodes. Circulation 1999;99:1312–1317.

18. Jenkins K J, Walsh E P, Colan S D, Bergau D M, Saul J P, Lock J E. Multipolar endocardial mapping of the right atrium during cardiac catheterization: description of a new technique. J Am Coll Cardial 1993;22:1105–1110.

19. Eldar M, Fitzpatrick A P, Ohad D, Smith M F, Hsu S, Whayne J G, Vered Z, Rotstein Z, Kordis T, Swanson D K, Chin M, Scheinman M M, Lesh M D, Greenspon A J. Percutaneous multielectrode endocardial mapping during ventricular tachycardia in the swine model. Circulation 1996;94:1125–1130.

20. Taccardi B, Arisi G, Macchi E, Baruffi S, Spaggiari S. A new intracavitary probe for detecting the site of origin of ectopic ventricular beats during one cardiac cycle. Circulation 1987;75:272–281.

21. Derfus D L, Pilkington T C, Simpson E W, Ideker R E. A comparison of measured and calculated intracavitary potentials for electrical stimuli in the exposed dog heart. IEEE Trans Biomed Eng 1992;39:1192–1206.

22. Hilger A L, Claydon F J, Ingram L A, Mirvis D M. Quantitative effects of acute myocardial infarction on intracavitary potentials. Proc 14th IEEE/EMBS 1992, pp 537–539.

23. Schilling R J, Peters N S, Davies D W. Simultaneous endocardial mapping in the human left ventricle using a noncontact catheter: Comparison of contact and reconstructed electrograms during sinus rhythm. Circulation 1998;98:887–898.

24. Barr R C, Spach M S. Inverse calculations of QRS-T epicardial potentials from body surface potential distributions for normal and ectopic beats in the intact dog. Circ Res 1978;42:661–675.

25. Colli-Franzone P, Guerri L, Tentoni S, Viganotti C, Baruffi S, Spaggiari S, Taccardi B. A mathematical procedure for solving the inverse problem of electrocardiography: analysis of the time-space accuracy from in vitro experimental data. Math Biosci 1985;77:353–396.

26. Durrer D, van Dam R T, Freud G E, Janse M J, Meijler F L, Arzbaecher R C. Total excitation of the isolated human heart. Circulation 1970;41:899–912.

27. Spach M S and Barr R C. Ventricular intramural and epicardial potential distribution during ventricular activation and repolarization in the intact heart. Circ Res 1975;37:243–257.

28. Messinger-Rapport B J, Rudy Y. Regularization of the inverse problem in electrocardiography: a model study. Math Biosci 1988;89:79–118.

29. Messinger-Rapport B J, Rudy Y. Computational issues of importance to the inverse recovery of epicardial potentials in a realistic heart-torso geometry. Math Biosci 1989;97:85–120.

30. Tikhonov A N, Arsenin V Y. Solutions of Ill-Posed Problems. Washington: V. H. Winston & Sons, 1977, pp 27–94.

31. Colli-Franzone P, Guerri L, Taccardi B, Viganotti C. Finite element approximation of regularized solutions of the inverse potential problem of electrocardiography and applications to experimental data. Calcolo 1985;22:91–186.

32. Messinger-Rapport B J, Rudy Y. Noninvasive recovery of epicardial potentials in a realistic heart-torso geometry. Normal sinus rhythm. Circ Res 1990;66:1023–1039.

33. Gulrajani R M. The forward and inverse problems of electrocardiography. IEEE Eng Med Biol 1998;17(5): 84–122.

34. MacLeod R S, Brooks D H. Recent progress in inverse problems in electrocardiology. IEEE Eng Med Biol 1998;17(1):73–83.

35. Iakovidis I and Gulrajani R M. Improving Tikhonov regularization with linearly constrained optimization: application to the inverse epicardial potential solution. Math Biosci 1992;112:55–80.

36. Oster H S, Rudy Y. Regional regularization of the electrocardiographic inverse problem: a model study using spherical geometry. IEEE Trans Biomed Eng 1997; 44:188–199.

37. Oster H S, Rudy Y. The use of temporal information in the regularization of the inverse problem of electrocardiography. IEEE Trans Biomed Eng 1992;39:65–75.

38. Greensite F and Huiskamp G. An improved method for estimating epicardial potentials from the body surface. IEEE Trans Biomed Eng 1998;45:98–104.

39. Khoury D S, Rudy Y. A model study of volume conductor effects on endocardial and intracavitary potentials. Circ Res 1992;71:511–525.

40. Khoury D S. Recovery of endocardial potentials from intracavitary potential data [Dissertation]. Cleveland, Ohio: Case Western Reserve University, 1993, 174 p.

41. Khoury D S, Rudy Y. Reconstruction of endocardial potentials from intracavitary probe potentials. A model study. Proc Comput Cardiol 1992, pp 9–12.

42. Khoury D S. Use of current density in the regularization of the inverse problem of electrocardiography. Proc 16th IEEE/EMBS 1994, pp 133–134.

43. Khoury D S, Marks G F. Adaptive regularization of the inverse problem in electrocardiography. Proc 17th IEEE/EMBS 1995 [CD ROM].

44. Khoury D S, Taccardi B, Lux R L, Ershler P R, Rudy Y. Reconstruction of endocardial potentials and excitation sequences from intracavitary probe measurements. Localization of pacing sites and effects of myocardial structure. Circulation 1995;91:845–863.

45. Khoury D S, Berrier K L, Badruddin S M, Zoghbi W A. Three-dimensional electrophysiologic imaging of the intact dog left ventricle using a noncontact multielectrode cavity probe. Study of sinus, paced, and spontaneous premature beats. Circulation 1998;97:399–409.

46. Velipasaoglu E O, Sun H, Berrier K L, Khoury D S. Spatial regularization of the electrocardiographic inverse problem and its application to endocardial mapping. IEEE Trans Biomed Eng 2000;47:327–337.
47. Sun H, Velipasaoglu E O, Berrier K L, Khoury D S. Electrophysiological imaging of the right atrium using a noncontact multielectrode cavitary probe: study of normal and abnormal rhythms. PACE 1998;21[Pt. II]:2500–2505.
48. Rao L, Sun H, Khoury D S. Global Comparisons between contact and noncontact mapping techniques in the right atrium: role of cavitary probe size. Submitted to Ann Biomed Eng.
49. Velipasaoglu E O, Berrier K L, Sun H, Khoury D S. Determining locations of intracardiac basket and probe electrodes from multiplane fluoroscopic images. Proc Comput Cardiol 1998;25:465–468.
50. Velipasaoglu E O, Sun H, Khoury D S. Reconstruction of endocardial multielectrode basket geometry from multiplane fluoroscopic images. Proc 1st Joint Mtg BMES and EMBS. Atlanta, Ga., 1999;276, CD ROM.
51. Schilling R J, Peters N S, Davies D W. Feasibility of a noncontact catheter for endocardial mapping of human ventricular tachycardia. Circulation 1999;99:2543–2552.
52. Brebbia C A, Dominguez J. Boundary Elements. An Introductory Course. Southampton and Boston: Computational Mechanics Publications, 1989, pp 45–132.
53. Macchi E, Arisi G, Taccardi B. Intracavitary mapping: an improved method for locating the site of origin of ectopic ventricular beats by means of a mathematical model. Proc 10th IEEE/EMBS 1988, pp 187–188.

MOST RELEVANT PUBLICATIONS

1. Taccardi B, Arisi G, Macchi E, Baruffi S, Spaggiari S. A new intracavitary probe for detecting the site of origin of ectopic ventricular beats during one cardiac cycle. Circulation 1987;75:272–281.
2. Gepstein L, Hayam G, Ben-Haim S A. A novel method for nonfluoroscopic catheter-based electroanatomical mapping of the heart. In vitro and in vivo accuracy results. Circulation 1997;95:1611–1622.
3. De Groot N M S, Bootsma M, Van Der Velde E T, Schalij M J. Three-dimensional catheter positioning during radiofrequency ablation in patients: first application of a real-time position management system. J Cardiovasc Electrophysiol 2000;11:1183–1192.
4. Wittkampf F H M, Wever E F D, Derksen R, Wilde A A M, Ramanna H, Hauer R N W, Robles de Medlina E O. LocaLisa. New technique for real-time 3-dimensional localization of regular intracardiac electrodes. Circulation 1999;99:1312–1317.
5. Jenkins K J, Walsh E P, Colan S D, Bergau D M, Saul J P, Lock J E. Multipolar endocardial mapping of the right atrium during cardiac catheterization: description of a new technique. J Am Coll Cardial 1993;22:1105–1110.
6. Eldar M, Fitzpatrick A P, Ohad D, Smith M F, Hsu S, Whayne J G, Vered Z, Rotstein Z, Kordis T, Swanson D K, Chin M, Scheinman M M, Lesh M D, Greenspon A J. Percutaneous multielectrode endocardial mapping during ventricular tachycardia in the swine model. Circulation 1996;94:1125–1130.
7. Derfus D L, Pilkington T C, Simpson E W, Ideker R E. A comparison of measured and calculated intracavitary potentials for electrical stimuli in the exposed dog heart. IEEE Trans Biomed Eng 1992;39:1192–1206.
8. Schilling R J, Peters N S, Davies D W. Simultaneous endocardial mapping in the human left ventricle using a noncontact catheter: Comparison of contact and reconstructed electrograms during sinus rhythm. Circulation 1998;98:887–898.
9. Ren J F, Schwartzman D, Callans D J, Brode S E, Gottlieb C D, Marchlinski F E. Intracardiac echocardiography (9 MHz) in humans: methods, imaging views and clinical utility. Ultrosound Med Biol 1999;25:1077–1086.
10. Ladd M E, Quick H H, Debatin J F. Interventional MRI and intravascular imaging. J Magn Reson Imaging 2000; 12:534–546.
11. Khoury D S. Recovery of endocardial potentials from intracavitary potential data [Dissertation]. Cleveland, Ohio: Case Western Reserve University, 1993, 174 p.
12. Khoury D S, Taccardi B, Lux R L, Ershler P R, Rudy Y. Reconstruction of endocardial potentials and excitation sequences from intracavitary probe measurements. Localization of pacing sites and effects of myocardial structure. Circulation 1995;91:845–863.
13. Khoury D S, Berrier K L, Badruddin S M, Zoghbi W A. Three-dimensional electrophysiologic imaging of the intact dog left ventricle using a noncontact multielectrode cavitary probe. Study of sinus, paced, and spontaneous premature beats. Circulation 1998;97:399–409.
14. Sun H, Velipasaoglu E O, Berrier K L, Khoury D S. Electrophysiological imaging of the right atrium using a noncontact multielectrode cavitary probe: study of normal and abnormal rhythms. PACE 1998;21[Pt. II]:2500–2505.
15. Velipasaoglu E O, Sun H, Berrier K L, Khoury D S. Spatial regularization of the electrocardiographic inverse problem and its application to endocardial mapping. IEEE Trans Biomed Eng 2000;47:327–337.
16. Khoury D S, Sun H, Velipasaoglu E O, Dupree D, McMillan A, Panescu D. Four-dimensional, biatrial mapping in the intact beating heart [Abstract]. PACE 2000; 23:750.
17. Rao L, Sun H, Khoury D S. Global Comparisons between contact and noncontact mapping techniques in the right atrium: role of cavitary probe size. Ann Biomed Eng 2001;29:493–500.
18. Khoury D S, Sun H, Velipasaoglu E O, Dupree D, McMillan A, Panescu D. Four-dimensional, biatrial mapping in the intact beating heart [Abstract]. Pacing and Clinical Electrophysiology (PACE) 2000;23:750. Presented as a poster at the 21st Annual Scientifc Sessions of the North American Society of Pacing and Electrophysiology, Washington, D.C.

What is claimed is:

1. A device for measuring electrical and geometric characteristics of body tissue from a blood-filled cavity within the tissue, comprising:

a multielectrode lumen catheter, having multiple electrodes arranged in a fixed pattern on a continuous surface, wherein the electrodes are configured to take multiple simultaneous non-contact measurements of electrical potentials resulting from electrical activity from multiple locations in the tissue; and an anatomical imaging catheter having at least one imaging element for visualizing anatomical characteristics located inside the multielectrode lumen catheter, wherein the anatomical imaging catheter is configured to take multiple non-contact measurements of anatomical characteristics of the tissue, and for determining location and orientation of the multielectrode catheter with respect to the tissue;

wherein the multielectrode catheter and the imaging catheter are configured to provide the measurements of electrical potentials and the measurements of anatomical characteristics to a data processing system for reconstruction of tissue surface electrograms.

2. The device of claim 1, further comprising a coaxial tube catheter located inside the multielectrode lumen catheter, wherein the coaxial tube catheter provides structural support to the multielectrode lumen catheter, and serves as a conduit for advancing or withdrawing the multielectrode lumen catheter over the surface of the coaxial tube catheter, and for advancing or withdrawing the anatomical imaging catheter within a lumen of the coaxial tube catheter.

3. The device of claim 2, wherein the tissue comprises heart tissue and wherein the anatomical imaging catheter comprises an ultrasound transducer, which in operation continually provides tomographic sections of the heart cavity.

4. The device of claim 2, wherein the tissue comprises heart tissue and wherein the multielectrode lumen catheter is receptive to continuous cavitary electrical potentials, for producing signals for displaying graphical isopotential and isochronal maps of the electrical characteristics of the heart tissue.

5. The device of claim 2, wherein a roving electrode-catheter is inserted into the tissue cavity through the center of the multielectrode catheter, and the roving catheter emits and receives a location signal for determining the position and shape of the roving catheter.

6. The device of claim 2, wherein the data processing system comprises a data acquisition system, a data analysis system, and a data display system coupled to the device,
wherein the data acquisition system is responsive to the multiple non-contact measurements of the electrical and anatomical characteristics to provide electrical and anatomical data to the data analysis system,
wherein the data analysis system is responsive to the electrical and anatomical data to reconstruct the tissue surface electrograms by solving Laplace's equation,
wherein Laplace's equation is solved by employing the boundary element method and numeric regularization, and
wherein the data display system is responsive to the tissue surface electrograms to depict three-dimensional electrical, anatomical, and functional characteristics of the tissue.

7. The device of claim 2, wherein a roving electrode-catheter is inserted into the tissue cavity through the center of the multielectrode catheter, and the roving catheter is navigated beyond the multielectrode catheter within a three-dimensional geometric model of the tissue cavity, wherein the model is numerically reconstructed on the basis of measurements of anatomical characteristics made using ultrasound, infrared, or magnetic resonance.

8. The device of claim 2, wherein the anatomical imaging catheter is configured to provide dimensions of the interior of the cavity.

9. The device of claim 2, wherein the anatomical imaging catheter is configured to provide distances between the multielectrode lumen catheter and the tissue interior.

10. The device of claim 2, wherein the anatomical imaging catheter comprises a position sensor.

11. The device of claim 1, wherein the data processing system comprises a data acquisition system, a data analysis system, and a data display system coupled to the device,
wherein the data acquisition system is responsive to the multiple non-contact measurements of the electrical and anatomical characteristics to provide electrical and anatomical data to the data analysis system,
wherein the data analysis system is responsive to the electrical and anatomical data to reconstruct the tissue surface electrograms by solving Laplace's equation,
wherein Laplace's equation is solved by employing the boundary element method and numeric regularization, and
wherein the data display system is responsive to the tissue surface electrograms to depict three-dimensional electrical, anatomical, and functional characteristics of the tissue.

12. The device of claim 1, wherein the tissue comprises heart tissue and wherein the anatomical imaging catheter comprises an ultrasound transducer, which in operation continually provides tomographic sections of the heart cavity.

13. The device of claim 1, wherein the tissue comprises heart tissue and wherein the multielectrode lumen catheter is receptive to continuous cavitary electrical potentials, for producing signals for displaying graphical isopotential and isochronal maps of the electrical characteristics of the heart tissue.

14. The device of claim 1, wherein a roving electrode-catheter is inserted into the tissue cavity through the center of the multielectrode catheter, and the roving catheter emits and receives a location signal for determining the position and shape of the roving catheter.

15. The device of claim 1, wherein a roving electrode-catheter is inserted into the tissue cavity through the center of the multielectrode catheter, and the roving catheter is navigated beyond the multielectrode catheter within a three-dimensional geometric model of the tissue cavity, wherein the model is numerically reconstructed on the basis of measurements of anatomical characteristics made using ultrasound, infrared, or magnetic resonance.

16. The device of claim 1, wherein the anatomical imaging catheter is configured to provide dimensions of the interior of the cavity.

17. The device of claim 1, wherein the anatomical imaging catheter is configured to provide distances between the multielectrode lumen catheter and the tissue interior.

18. The device of claim 1, wherein the anatomical imaging catheter comprises a position sensor.

19. A method for measuring electrical and geometric characteristics of body tissue from a blood-filled cavity within the tissue, comprising:
inserting into the cavity a multielectrode catheter having multiple electrodes arranged in a fixed pattern on a continuous surface;
inserting through the multielectrode catheter and into the cavity an anatomical imaging catheter having at least one imaging element for visualizing anatomical characteristics;
determining location and orientation of the multielectrode catheter with respect to the tissue using the imaging catheter;
taking multiple simultaneous non-contact measurements of electrical potentials resulting from electrical activity from multiple locations in the tissue using the multielectrode catheter;
taking multiple non-contact measurements of anatomical characteristics of the tissue using the imaging catheter; and
reconstructing tissue surface electrograms based on the determined location and orientation of the multielectrode catheter with respect to the tissue, the measured electrical potentials and the measured anatomical characteristics.

20. The method of claim 19, wherein taking multiple non-contact measurements of anatomical characteristics of the tissue comprises recording continuous anatomical images using the anatomical imaging catheter while the heart beats.

21. The method of claim 20, further comprising inserting a roving electrode-catheter into the tissue cavity through the center of the multietectrode catheter, and navigating the roving catheter beyond the multielectrode catheter within a three-dimensional geometric model of the tissue cavity, wherein the model is numerically reconstructed on the basis of measurements of anatomical characteristics made using ultrasound, infrared, or magnetic resonance.

22. The method of claim 20, wherein reconstructing the tissue surface electrograms comprises sending the multiple non-contact measurements of the electrical potentials and anatomical characteristics to a data processing system and reconstructing the tissue surface electrograms in the data processing system.

23. The method of claim 22, wherein reconstructing the tissue surface electrograms comprises numerically reconstructing three-dimensional electrical characteristics of the tissue by solving Laplace's equation based on the measurements of the electrical potentials and anatomical characteristics, and employing the boundary element method and numeric regularization.

24. The method of claim 20, wherein taking multiple non-contact measurements of the anatomical characteristics is performed using ultrasound, infrared, or magnetic resonance.

25. The method of claim 20, further comprising inserting a roving electrode-catheter through the center of the multielectrode catheter, and navigating the roving electrode-catheter beyond the multielectrode catheter in the cavity based on the measurements of the anatomical characteristics.

26. The method of claim 20, wherein the anatomical imaging catheter comprises an ultrasound transducer and wherein recording continuous anatomical images comprises continually provides tomographic sections of the cavity.

27. The method of claim 20, further comprising the multielectrode catheter receiving continuous cavitary electrical potentials, and producing signals to display graphical isopotential and isochronal maps of the electrical characteristics of the tissue.

28. The method of claim 20, further comprising inserting a roving electrode-catheter into the cavity through the center of the multielectrode catheter, and the roving catheter emitting and receiving a location signal for determining the position and shape of the roving catheter.

29. The method of claim 20, further comprising the anatomical imaging catheter providing dimensions of the interior of the cavity.

30. The method of claim 20, further comprising the anatomical imaging catheter providing distances between the multielectrode lumen catheter and the tissue interior.

31. The method of claim 20, further comprising the step of sensing the position of the anatomical imaging catheter.

32. The method of claim 19, wherein the cavity comprises a chamber of a human heart and wherein inserting the multielectrode catheter and the imaging catheter into the cavity comprise:
 inserting a coaxial tube catheter into a blood vessel of a human;
 sliding the coaxial tube catheter through the blood vessel and into the heart chamber;
 sliding the multielectrode catheter over the outside surface of the coaxial tube catheter and into the heart chamber;
 sliding the anatomical imaging catheter through the interior of the coaxial tube catheter and into the heart chamber.

33. The method of claim 32, wherein taking multiple non-contact measurements of anatomical characteristics of the tissue comprises recording continuous anatomical images using the anatomical imaging catheter while the heart beats.

34. The method of claim 33, wherein the anatomical imaging catheter comprises an ultrasound transducer and wherein recording continuous anatomical images comprises continually provides tomographic sections of the cavity.

35. The method of claim 33, further comprising the multielectrode catheter receiving continuous cavitary electrical potentials, and producing signals to display graphical isopotential and isochronal maps of the electrical characteristics of the tissue.

36. The method of claim 33, further comprising inserting a roving electrode-catheter into the cavity through the center of the multielectrode catheter, and the roving catheter emitting and receiving a location signal for determining the position and shape of the roving catheter.

37. The method of claim 33, further comprising inserting a roving electrode-catheter into the tissue cavity through the center of the multietectrode catheter, and navigating the roving catheter beyond the multielectrode catheter within a three-dimensional geometric model of the tissue cavity, wherein the model is numerically reconstructed on the basis of measurements of anatomical characteristics made using ultrasound, infrared, or magnetic resonance.

38. The method of claim 33, wherein reconstructing the tissue surface electrograms comprises sending the multiple non-contact measurements of the electrical potentials and anatomical characteristics to a data processing system and reconstructing the tissue surface electrograms in the data processing system.

39. The method of claim 38, wherein reconstructing the tissue surface electrograms comprises numerically reconstructing three-dimensional electrical characteristics of the tissue by solving Laplace's equation based on the measurements of the electrical potentials and anatomical characteristics, and employing the boundary element method and numeric regularization.

40. The method of claim 33, wherein taking multiple non-contact measurements of the anatomical characteristics is performed using ultrasound, infrared, or magnetic resonance.

41. The method of claim 40, further comprising inserting a roving electrode-catheter through the center of the multielectrode catheter, and navigating the roving electrode-catheter beyond the multielectrode catheter in the cavity based on the measurements of the anatomical characteristics.

42. The method of claim 33, further comprising the anatomical imaging catheter providing dimensions of the interior of the cavity.

43. The method of claim 33, further comprising the anatomical imaging catheter providing distances between the multielectrode lumen catheter and the tissue interior.

44. The method of claim 33, further comprising the step of sensing the position of the anatomical imaging catheter.

* * * * *